United States Patent
Yin et al.

(10) Patent No.: US 9,237,873 B2
(45) Date of Patent: Jan. 19, 2016

(54) METHODS AND SYSTEMS FOR CT PROJECTION DOMAIN EXTRAPOLATION

(75) Inventors: Zhye Yin, Schenectady, NY (US); Paulo Ricardo Mendonca, Clifton Park, NY (US); Bruno Kristiaan Bernard De Man, Clifton Park, NY (US); Kai Zeng, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 838 days.

(21) Appl. No.: 13/285,953

(22) Filed: Oct. 31, 2011

(65) Prior Publication Data

US 2013/0108007 A1    May 2, 2013

(51) Int. Cl.
A61B 6/02 (2006.01)
A61B 6/03 (2006.01)
A61B 6/00 (2006.01)
G06T 11/00 (2006.01)

(52) U.S. Cl.
CPC .......... *A61B 6/032* (2013.01); *A61B 6/5205* (2013.01); *A61B 6/5258* (2013.01); *G06T 11/005* (2013.01); *G06T 2211/432* (2013.01)

(58) Field of Classification Search
CPC .... A61B 6/5205; A61B 6/032; A61B 6/5258; G06T 11/005; G06T 2211/432
USPC .............................................. 378/4; 382/131
See application file for complete search history.

(56) References Cited

U.S. PATENT DOCUMENTS

| | | | |
|---|---|---|---|
| 5,953,388 A | 9/1999 | Walnut et al. | |
| 6,084,936 A | 7/2000 | Patch | |
| 6,307,909 B1 | 10/2001 | Flohr et al. | |
| 6,987,520 B2 | 1/2006 | Criminisi et al. | |
| 7,440,535 B2 | 10/2008 | Netsch et al. | |
| 7,660,379 B2 | 2/2010 | Scholz | |
| 2004/0066909 A1* | 4/2004 | Lonn et al. | 378/901 |
| 2010/0283779 A1 | 11/2010 | Chiang et al. | |

FOREIGN PATENT DOCUMENTS

JP    2009279301 A  * 12/2009

OTHER PUBLICATIONS

PTO 14-2635 which is an English language translation of JP02009279301A.*
Sadowsky et al., Hybrid Cone-Beam Tomographic Reconstruction: Incorporation of Prior Anatomical Models to Compensate for Missing Data, Published electronically on Jul. 26, 2010, IEEE Transactions on Medical Imaging, vol. 30, No. 1, pp. 69-83.*

(Continued)

*Primary Examiner* — David J Makiya
*Assistant Examiner* — John Corbett
(74) *Attorney, Agent, or Firm* — Robert M. McCarthy

(57) ABSTRACT

A system and method for CT projection extrapolation are provided. The method comprises receiving a CT projection for extrapolation. The method also comprises selecting a target patch comprising at least one pixel of a row to be extrapolated. The method further comprises generating a correlation profile between the target patch and one or more source patches, wherein the source patches comprise measured pixels in the CT projection in one or more rows adjacent to the target patch. The projection data is generated for at least one pixel of the target patch based on the correlation profile and the measured pixels of at least one of the source patches.

27 Claims, 8 Drawing Sheets

(56) References Cited

OTHER PUBLICATIONS

Sadowsky ("Image Registration and Hybrid Volume reconstruction of Bone Anatomy Using a statistical Shape Atlas" 2008, Doctoral Dissertation, Johns Hopkins University.*

Tiwari et al. ("Solving a part classification problem using simulated annealing-like hybrid algorithm", 2003, Robotics and Computer Integrated Manufacturing, vol. 19, pp. 415-424.*

Mendonca et al., A Dynamic-programming Projection-domain Extrapolation Method for CT Wide-Cone Reconstruction, Presented Dec. 5, 2013, 99th Scientific Assembly and Annual Meeting of the Radiological Society of North America (RSNA 2013), Abstract No. LL-PHS-TH5B, 1 page.*

Nett, Three Dimensional Image Guided Extrapolation for Cone-Beam CT Image Reconstruction, 2014, SPIE vol. 9033, pp. 20-1 to 20-8.*

Zamyatin et al., Extension of the reconstruction field of view and truncation correction using sinogram decomposition, 2007, Medical Physics, vol. 34, No. 5, pp. 1593-1604.*

Kostler et al., Adaptive variational sinogram interpolation of sparsely sampled CT data, 2006, Pattern Recognition 2006, 18th International Conference on the ICPR 2006, vol. 3, pp. 778-781.*

Kalke et al., Sinogram Interpolation Method for Sparse-Angle Tomography, 2014, Applied Mathematics, vol. 5, pp. 423-441.*

Van Gompel, Towards accurate image reconstruction from truncated X-ray CT projections, 2009, Universiteit Antwerpen doctoral dissertation, 146 pages.*

Chityala et al., Artifact reduction in truncated CT using Sinogram completion, 2005, SPIE, vol. 5747, pp. 2110-2117.*

Herraiz et al., Frequency Selective Signal Extrapolation for Compensation of Missing Data in Sinograms, 2008, IEEE, 2008 IEEE Nuclear Science Symposium Conference Record, Paper No. M06-423, pp. 4299-4302.*

Joseph Shtok et al.; Spatially-Adaptive Reconstruction in Computed Tomography Based on Statistical Learning; Computing Research Repository; 2010; 12 Pages.

Jian Fu et al.; Methods Determining the Angular Increment of a Continuous Scan Cone-Beam CT System; IEEE Transactions on Nuclear Science, vol. 57, No. 3, June 2010; pp. 1071-1076.

Ilknur Kabul et al.; Model-based Solid Texture Synthesis for Anatomic Volume Illustration; Eurographics Workshop on Visual Computing for Biology and Medicine (Jul. 2010); 8 Pages.

* cited by examiner

METHODS AND SYSTEMS FOR CT PROJECTION DOMAIN EXTRAPOLATION

BACKGROUND

Embodiments presented herein relate generally to computerized tomography (CT) systems, and more particularly to systems and methods for processing sinograms obtained in CT systems.

CT or computerized axial tomography (CAT) is a medical imaging technique employing tomography generated by computer processing. CT imaging provides cross-sectional images or "slices" of anatomy. CT systems produce images using X-rays, based on the ability of various anatomical structures to block or absorb X-rays.

Conventional CT imaging systems comprise a motorized patient bed to advance the patient into a circular patient bore in the CT imaging system. As the patient passes through the CT imaging system, an X-ray emitter rotates around the inside of the patient bore. The X-ray emitter emits a narrow, cone-shaped beam of X-rays to irradiate a section of the patient's body. X-ray detectors on the opposite side of the X-ray emitter record the X-rays exiting the patient's body, thus forming an X-ray view at one angle of the X-ray emitter. Multiple such views are collected to produce a complete CT sinogram.

Once the sinogram data has been acquired, an image processor reconstructs the individual views into a cross-sectional slice of internal organs and tissues within the anatomical structure. Typically, the sinogram data of the individual slices is integrated to generate a three dimensional volumetric information (3D-CT scan). Such a 3D-CT scan is viewable from multiple different perspectives.

Accurate CT reconstruction is difficult due to a number of reasons. For example, in cone beam CT some sections of the patient's body are sometimes inside and sometimes outside the emitted X-ray beam, resulting in truncation of the projection at the edges. Such truncation is known as z-truncation. Z-truncation results in deterioration in image quality at the edges of reconstructed volume, and generates undesired artifacts. To mitigate artifacts generated due to z-truncation, data extrapolation techniques are required. One known technique of extrapolation estimates the truncated data by simple duplication extrapolation. In other words, the duplication extrapolation technique copies the first or last row of the available scan data to synthesize extra projection rows. However, such a technique may introduce inconsistencies between different views of the scan data and may result in false anatomic structures or streaks in the reconstructed images.

Therefore, there is a need for a system and a method that overcomes these and other disadvantages associated with known CT reconstruction techniques.

BRIEF DESCRIPTION

In accordance with various embodiments, a method for CT projection extrapolation is provided. The method comprises receiving, at an extrapolation processor, a CT projection for extrapolation. The method also comprises selecting a target patch comprising at least one pixel of a row to be extrapolated. Unknown values of pixels to be extrapolated are initialized by neighbouring values or zeros. The method further comprises generating a correlation profile between the target patch and one or more source patches, wherein the source patches comprise measured pixels in the CT projection in one or more rows adjacent to the target patch. Furthermore, the method comprises generating projection data for at least one pixel of the target patch based on the correlation profile and the measured pixels of at least one of the source patches.

In accordance with other various embodiments, a system for CT sinogram extrapolation is provided that comprises at least one processor. The system comprises computer program code stored in a non-transitory computer readable storage medium, wherein the computer program code, when executed, is operative to cause at least one processor to receive a CT projection for extrapolation, select a target patch comprising at least one pixel of a row to be extrapolated, and generate a correlation profile between the target patch and one or more source patches, wherein the source patches comprise measured pixels in the CT projection in one or more rows adjacent to the target patch. The processor is further configured to generate projection data for at least one pixel of the target patch based on the correlation profile and the measured pixels of at least one of the source patches.

In accordance with other various embodiments, a computer program product is provided that comprises a non-transitory computer readable medium encoded with computer-executable instructions for extrapolating CT projections, wherein the computer-executable instructions, when executed, cause one or more processors to: receive a CT projection for extrapolation, select a target patch comprising at least one pixel of a row to be extrapolated, generate a correlation profile between the target patch and one or more source patches, wherein the source patches comprise measured pixels in the CT projection in one or more rows adjacent to the target patch. The processor is further configured to generate projection data for at least one pixel of the target patch based on the correlation profile and the measured pixels of at least one of the source patches.

DETAILED DESCRIPTION

Figure 1:
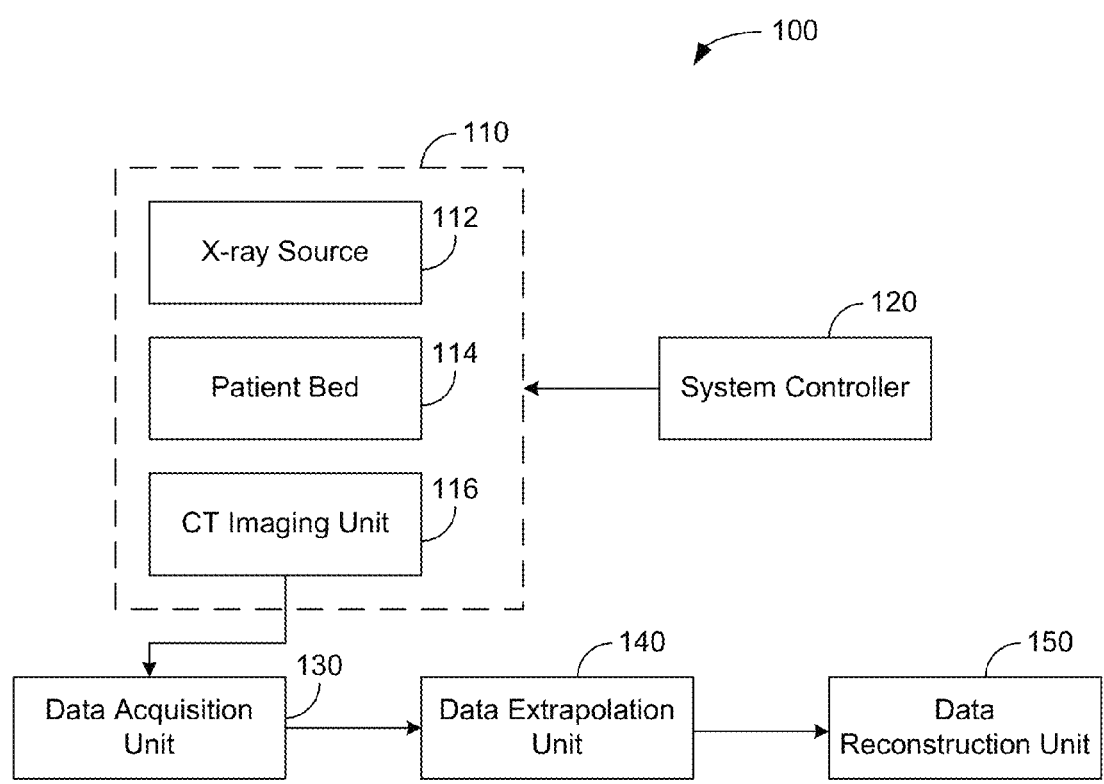
FIG. 1 illustrates a simplified block diagram of a CT imaging system, according to one embodiment.

To the extent that the figures illustrate diagrams of the functional blocks of various embodiments, the functional blocks are not necessarily indicative of the division between hardware. Thus, for example, one or more of the functional blocks may be implemented in a single piece of hardware or multiple pieces of hardware. It should be understood that the various embodiments are not limited to the arrangements and instrumentality shown in the drawings. Additionally, the system blocks in the various figures or the steps of the methods may be rearranged or reconfigured. Also, the steps of the various methods may be modified and performed in a different order or repeated as desired or needed.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may comprise additional such elements not having that property.

Various embodiments provide systems and methods for reconstructing CT sinogram data, and in particular, reconstructing CT sinogram data using extrapolation techniques. Reconstructed CT sinogram data may be used for obtaining information regarding the structural and functional details of the human organs.

FIG. 1 illustrates a simplified block diagram of a computerized tomography (CT) imaging system 100, according to one embodiment. The CT imaging system 100 comprises a CT gantry 110, a system controller 120, a data acquisition unit 130, a sinogram extrapolation unit 140, and a reconstruction and storage unit 150.

The CT gantry 110 further comprises an X-ray source 112, and an X-ray detector unit 114. The CT gantry 110 performs a CT scan of a patient laid on a patient bed 116. In some embodiments, the patient bed 116 is progressed linearly through the CT gantry 110 while the CT gantry 110 is fixed in position. In some other embodiments, the patient bed 116 is stationary while the CT gantry 110 moves over the length of the patient bed 116. FIG. 1 illustrates an embodiment where the patient bed 116 is progressed through the CT gantry 110.

The patient bed 116 comprises a sliding assembly to progress through the CT gantry 110. The X-ray source 112 and the X-ray detector unit 114 are arranged diametrically opposite to one another. The X-ray source 112 and the X-ray detector unit 114 are arranged such that they can rotate about an axis of the CT gantry 110, thus imaging the patient from multiple angles. Using the arrangement of the X-ray source and the X-ray detector, data representing cone beam projection of the subject may be obtained. Such a cone beam projection provides a 2D projection image of a 3D subject.

The X-ray source 112 generates a cone beam of X-rays. The X-ray source 112 may emit the X-rays continuously or intermittently at fixed intervals. The X-ray source 112 may comprise a shutter or collimator to control the beam width of the emitted cone beam.

The X-ray detector unit 114 comprises one or more detector elements. Typically the X-ray detector unit 114 comprises a plurality of detector elements arranged in an arc (for instance, a 50 degree arc) diametrically opposite the X-ray source 112. The X-ray detector unit 114 may comprise a linear array of detector elements, or a two-dimensional array of detector elements. Further, the X-ray detector unit 114 may comprise a uniform array of detector elements, a variable array of detector elements, or a hybrid array of detector elements. The X-ray detector unit 114 detects the X-rays that pass through the patient, and provides the detected signal to the data acquisition unit 130.

The system controller 120 controls the operation of various components of the CT imaging system 100. The system controller 120 may control the power, timing, and emissions of the X-ray source 112. The system controller 120 may also control the rotation of the CT gantry 110. Further, the system controller 120 may also control the rate of progression of the patient bed 116 through the CT gantry 110. The system controller 120 typically also controls the transfer of data from the X-ray detector unit 114 to the data acquisition unit 130. In one embodiment, the system controller 120 may synchronously control the X-ray source 112 and patient bed 116 such that CT gantry 110 executes circle scans and/or line scans of the patient, as per the diagnostic requirement. The circle scan and the line scan may be performed one after the other, in any order, again, as per the diagnostic requirements.

The output signal of X-ray detector unit 114 is transmitted to the data acquisition unit 130. The data acquisition unit 130 generates a CT sinogram based on the detected X-rays. The CT sinogram comprises a number of views or projections. Each view has a transaxial dimension and a longitudinal dimension that correspond to the number of columns and rows, respectively, of the X-ray detector unit 114. The CT sinogram represents the spatial distribution of the X-ray attenuation coefficient within the patient. Typically, the CT sinogram represents the spatial distribution of the X-ray attenuation coefficient over the full rotation of the CT gantry 110. As the CT gantry 110 rotates to image the patient from different angles, at each angle one CT projection is generated. One complete rotation of the CT gantry 110 may thus produce multiple CT projections, collectively forming CT sinograms, which may be reconstructed to the volume of interest.

In one embodiment, data acquisition unit processes the received signal, to produce projection data, such as line projection data, during a line scan, and circle projection data during a circle scan. The projection data may be pre-processed to calibrate system characteristics and to compensate for various physical effects. Examples of pre-processing includes, without limitation, detector corrections, incident intensity calibration, and de-blurring corrections.

Due to the geometry of the detector, some of the projection data generated by the data acquisition unit 130 may be truncated near the edges of the volume of interest. Often the scanned patient or object is "long" such that the shadow due to the cone beam extends outside the longitudinal dimension of a view. Therefore, the measured CT projection is extrapolated to mitigate artifacts caused due to z-truncation. For this, the received projection data is output from the data acquisition unit to a data extrapolation unit 140. The data extrapolation unit 140 processes the received projection data to generate extrapolated data corresponding to truncated portions of the projection data. In various embodiments, the data extrapolation unit 140 employs correlation-based extrapolation techniques to generate extrapolated data. An extrapolation processor may be housed within the data extrapolation unit 140 to facilitate the generation of extrapolated data.

The extrapolated data may be sent to a data reconstruction unit 150 to generate a volume image of the subject. The data reconstruction unit 150 combines the measured projection data with the extrapolated data to obtain a volume image. The reconstructed volume image may be sent to a display unit (not shown), where it may be displayed as a three-dimensional image or tomographic image. Although the various embodiments have been described using a particular imaging system to generate CT sinogram, for example, using a particular arrangement of different units, variations and modifications are contemplated.

Any suitable recording medium such as, but not limited to, an electronic solid-state device, a photographic film, or some other device such as a photo stimulable phosphor may be used for recording the projection data. The recorded data may be converted into digital form by a combination of electronic (as in the case of a CCD signal) or mechanical/optical means (as in the case of digitizing a photographic film or digitizing the data from a photo stimulable phosphor).

Figure 2:
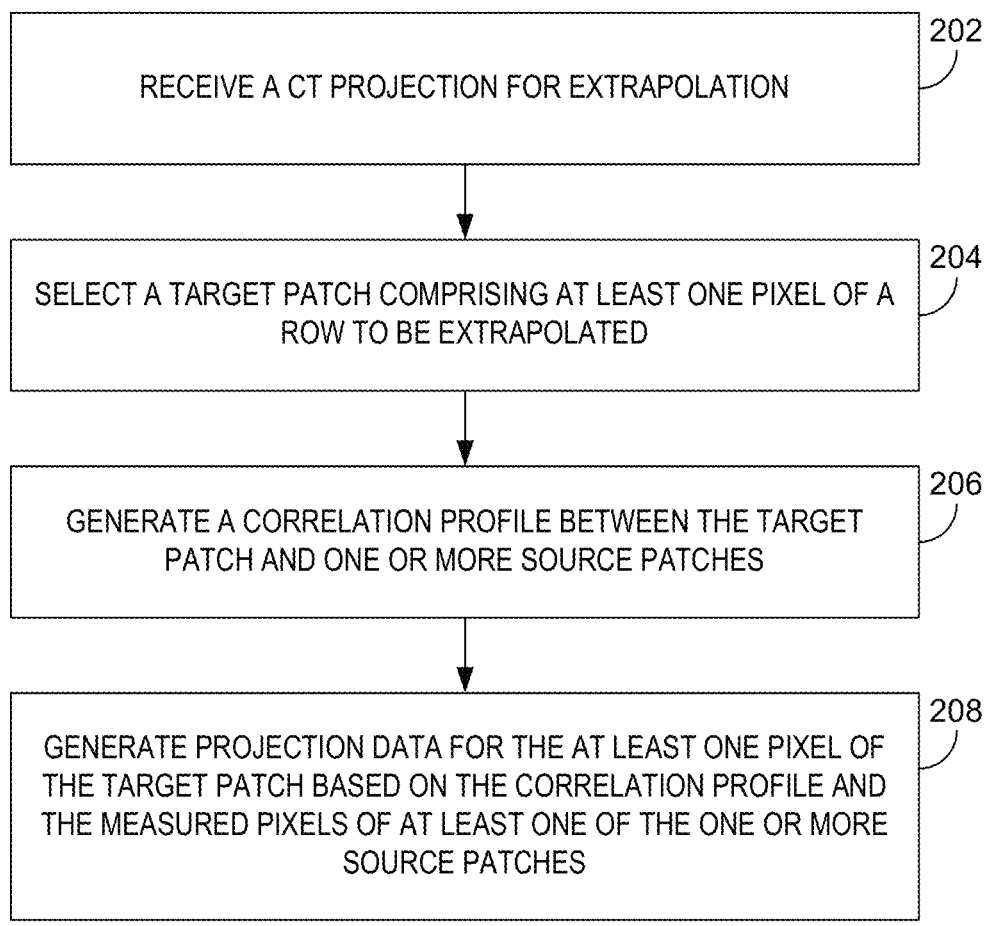
FIG. 2 is a flowchart illustrating an example process of sinogram extrapolation, according to one embodiment.

FIG. 2 illustrates the flowchart of an example process 200 of CT projection extrapolation, according to one embodiment. The process 200 extrapolates the measured or available projection data, thus generating additional projection data to reduce or eliminate altogether the longitudinal truncation of the CT projection. Subsequently, a complete volume image of the subject may be obtained by combining the measured sinogram data and the extrapolated sinogram data. The data extrapolation unit 140 may extrapolate each CT projection, while maintaining consistency with CT projections of other views of the same slice.

At step 202, the data extrapolation unit 140 receives a CT projection. The CT projection comprises a group of pixels. The CT projection may be divided into rows and columns, pixels, patches, tiles or regions. The received CT projection may suffer from z-truncation. The data extrapolation unit 140 may also receive a parameter defining the extent of z-truncation, or the expected dimension of a complete CT projection. The data extrapolation unit 140 may also compute the number of rows required to be extrapolated such that a complete CT projection is obtained for reconstruction.

In process 200, a CT projection may be divided into source and target patches. Target patch represents data from the CT projection that comprises at least one pixel from a row to be extrapolated and source patch represents data from the rows adjacent to the target patch that may be used for filling the target patch. Typically, within CT projections, there is a small likelihood of finding similar anatomical structures spatially distant from the target patch. Therefore, in various embodiments, the search for the missing pixel values is limited to a region spatially proximate to the target patch. In one embodiment, source patch comprises data that is within a predetermined number of rows from the target patch.

At step 204, the data extrapolation unit 140 selects a target patch comprising at least one pixel of the row to be extrapolated. The target patch may be an entire row, part of a row, a linear block of pixels, a two dimensional block of pixels, or simply one pixel.

In some embodiments, the data extrapolation unit 140 may initialize the target patch using, for example, nearest neighbor extrapolation. The data extrapolation unit 140 may initialize the target patch by copying pixel data from pixels in the vicinity of the target patch onto those pixels of the target patch that do not have CT measurement data. For instance, nearest neighbor extrapolation involves replacing pixels of the target patch that do not have CT measurement data with spatially closest pixels of the received CT projection. Such an initialized target patch may serve as a starting point for correlation based extrapolation.

Additionally, in some embodiments, the data extrapolation unit 140 may select the order in which the target patches are extrapolated, to ensure continuity of linear structures and composite textures. Since this approach fills patches of pixels instead of an individual pixel, filling order is important. The filling order of patches may be prioritized based on how strong the gradients are (measured using, for instance, a data term of the correlation profile) and how reliable a given patch is (measured using, for instance, a confidence term of the correlation profile). Target patches with more pixels from source region are surrounded by high-confidence pixels and may thus have higher priority in the filling order. Similarly, target patches with strong edges (e.g. strong gradient) may also have a higher priority in the filling order. In various implementations, where the target patch is a one dimensional row vector and initialized with a duplicate of previous row using the simplest extrapolation, the z gradient in a targeted region may be zero. In such implementations, the priority function for filling order might only consider column gradients and associated confidence terms.

At step 206, the data extrapolation unit 140 generates a correlation profile between the target patch and one or more source patches. The source patches may be an entire row, part of a row, a linear block of pixels, or a two dimensional block of pixels. The source patches may be located in the vicinity of the target patch. For example, the source patches may comprise measured pixels in the CT projection in one or more rows adjacent to the target patch. Typically, for a CT projection, the likelihood of finding a similar anatomical structure spatially distant from the target patch is low. Therefore, the data extrapolation unit 140 selects the source patches having measured pixels located in the rows adjacent to the target patch.

The data extrapolation unit 140 computes a correlation profile between the target patch and the source patches. The correlation profile represents the degree of similarity between the target patch and the source patches. The correlation profile may represent the spatial correlation between the target patch and the source patches. Alternatively, the correlation profile may represent a joint spatial and intensity correlation between the target patch and the source patches.

Figure 3:
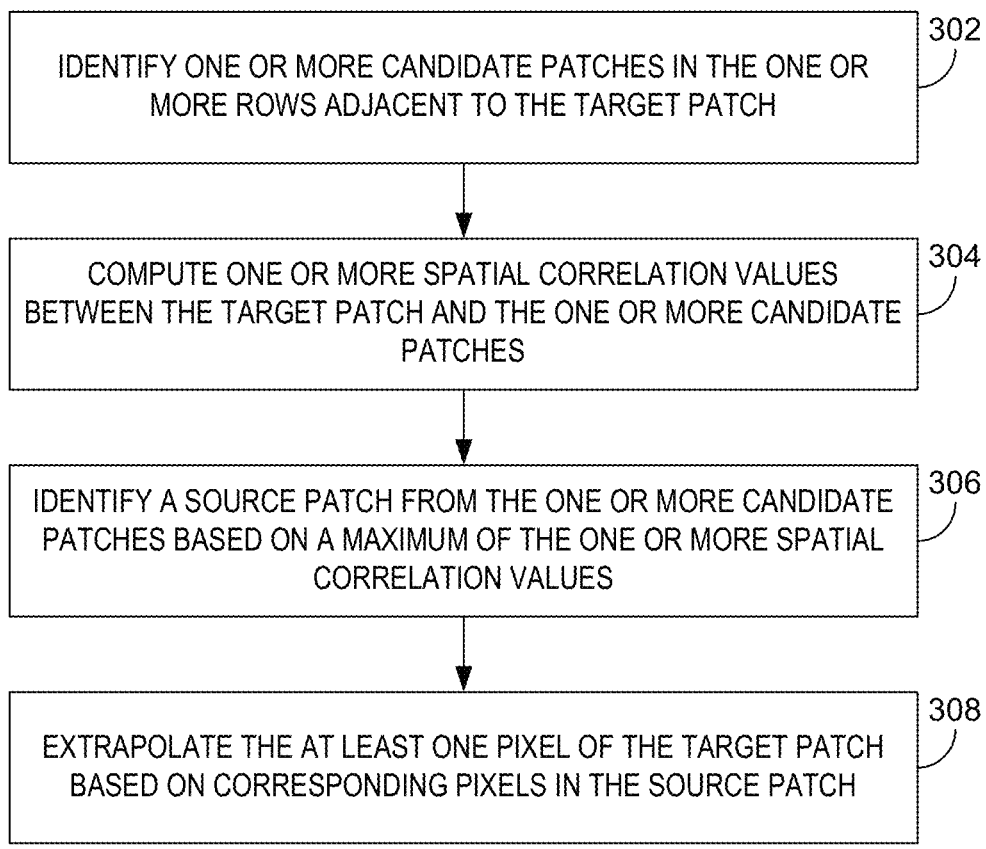
FIG. 3 is a flowchart illustrating an example process of projection extrapolation, according to another embodiment.
Figure 4:
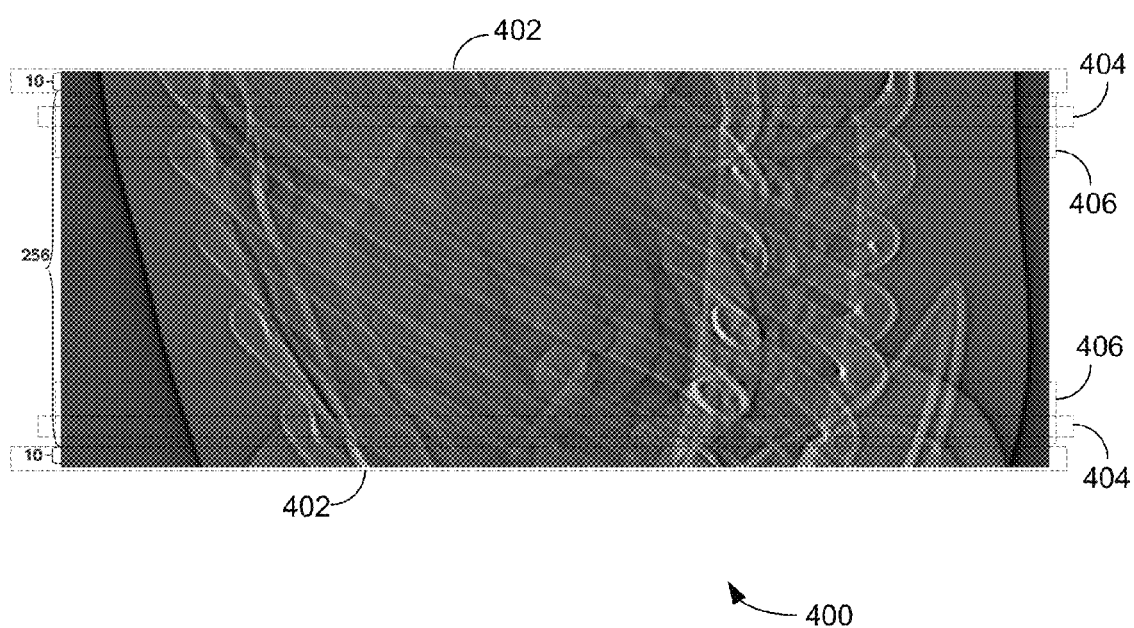
FIG. 4 illustrates example candidate, source, and target patches used for projection extrapolation, according to one embodiment.

Various techniques may be used to generate the correlation profile. In one implementation, the data extrapolation unit 140 identifies one or more candidate patches in the rows adjacent to the target patch. Thereafter, the data extrapolation unit 140 generates the correlation profile by computing spatial correlation values between the target patch and each of the candidate patches. Such an implementation is shown in FIGS. 3 and 4.

Figure 5:
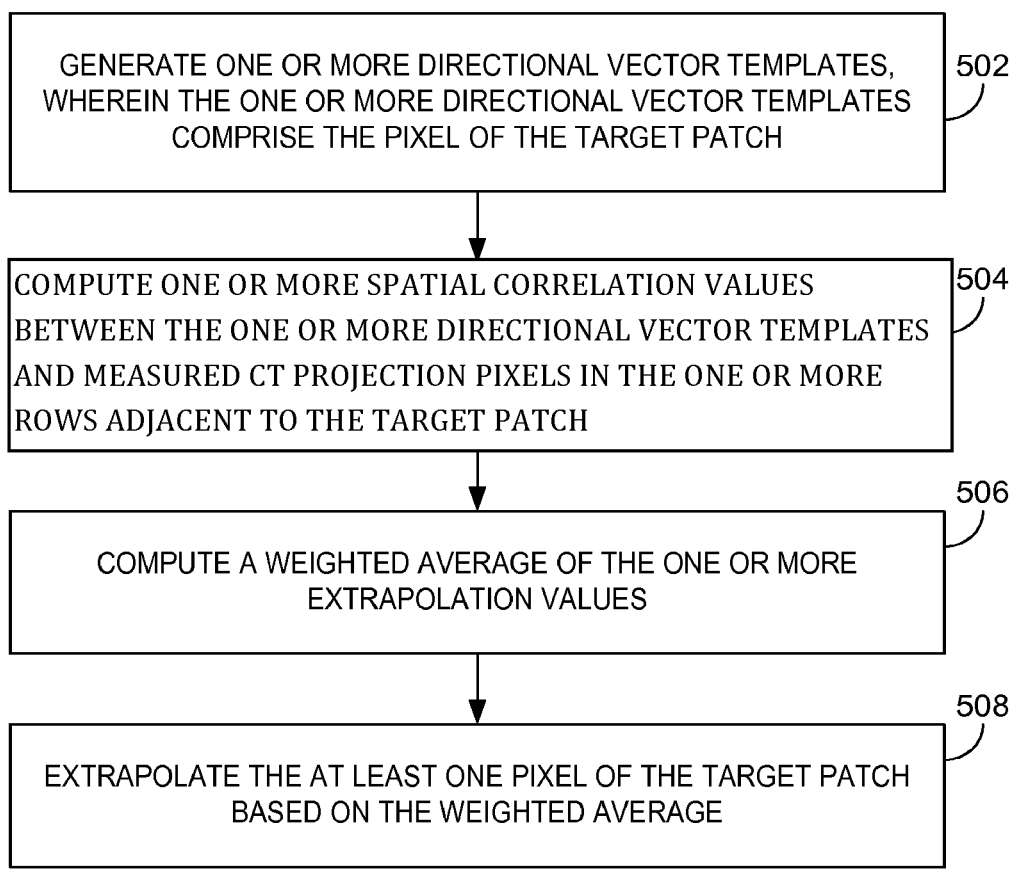
FIG. 5 is a flowchart illustrating an example process of projection extrapolation, according to another embodiment.
Figure 6:
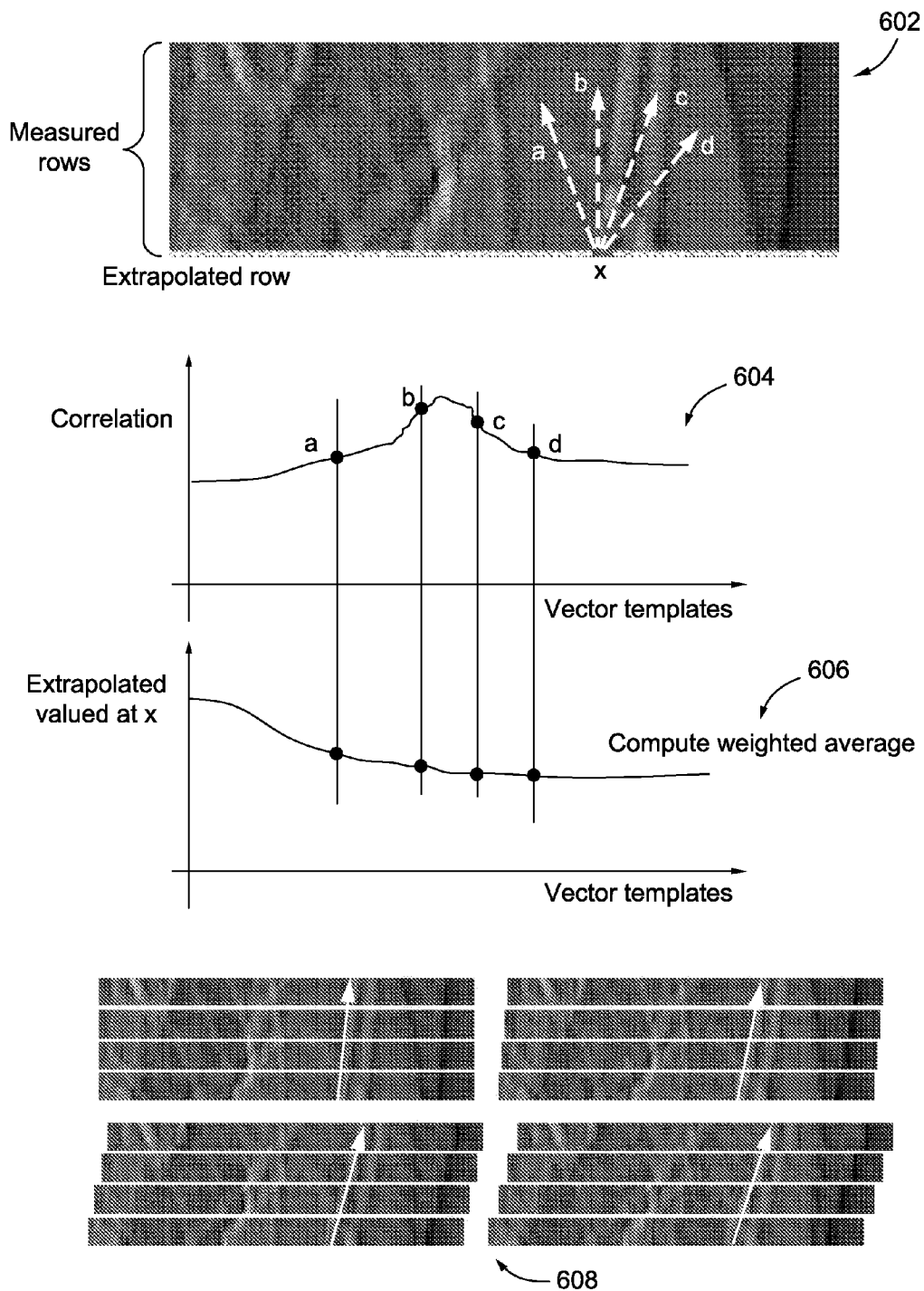
FIG. 6 illustrates example projection extrapolation using directional vector templates, according to another embodiment.

In another implementation, the data extrapolation unit 140 generates directional vector templates for a pixel of the target patch. The data extrapolation unit 140 generates the correlation profile for the pixel by computing spatial correlation values between the directional vector templates and the source patches. The source patches may be linear (one dimensional) blocks of pixels oriented in the direction of the directional vector templates. Such an implementation is shown in FIGS. 5 and 6.

Figure 7:
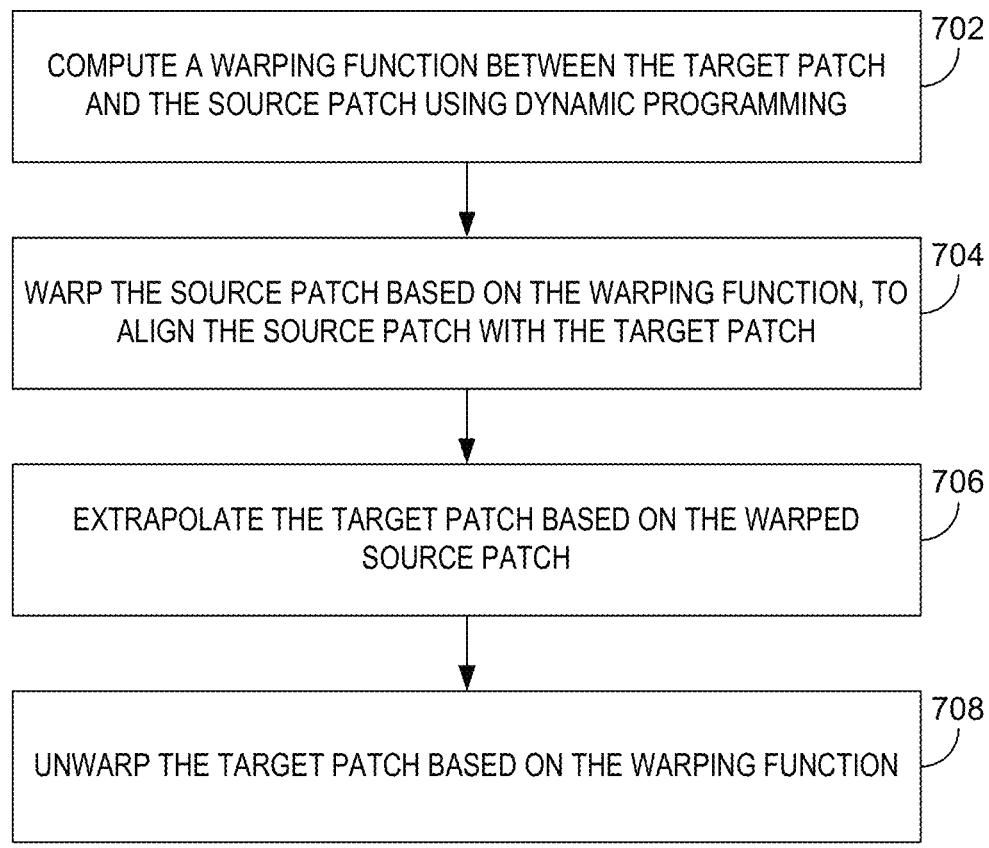
FIG. 7 is a flowchart illustrating an example process of projection extrapolation, according to another embodiment.
Figure 8:
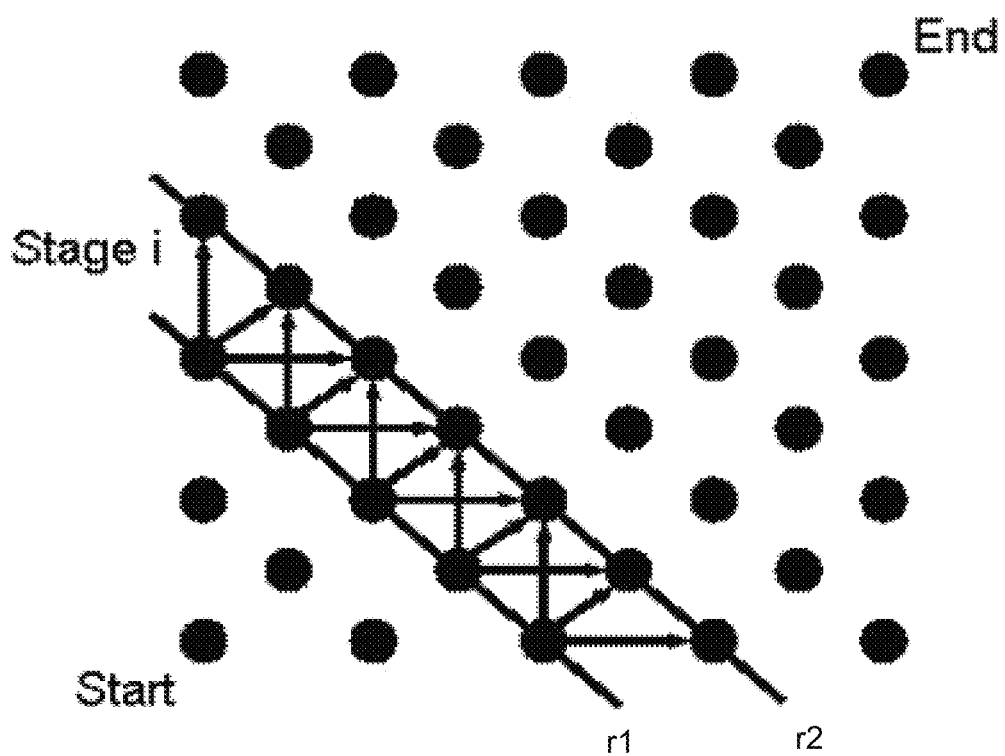
FIG. 8 illustrates an example process using a warping function for projection sinogram extrapolation, according to another embodiment.

In another implementation, the data extrapolation unit 140 generates the correlation profile by computing a warping function between the source patches and the target patches. The source patches and target patches may be complete or partial rows. Dynamic programming methods may be used to compute the warping function. Such an implementation is shown in FIGS. 7 and 8.

At step 208, the data extrapolation unit 140 generates projection data for at least one pixel of the row to be extrapolated based on the correlation profile and the measured projection data from the source patches. Thus, pixel data from the source patches is used to extrapolate the pixels of the target patch. The data extrapolation unit 140 may directly copy pixel data from the source patch to the target patch. Alternatively, the data extrapolation unit 140 may apply intensity scaling to the pixel of the source patch that corresponds to the pixel of the target patch being extrapolated. The data extrapolation unit 140 may copy the intensity scaled pixel data from the source patch to the target patch. The data extrapolation unit 140 may apply the intensity scaling based on the correlation profile.

In various embodiments, steps 202 through 208 may be repeated for all target patches. Further, the extrapolated CT projection data may be combined with the measured CT projection data to obtain a complete CT projection.

FIG. 3 is a flowchart illustrating an example process of projection extrapolation, according to another embodiment. The process 300 may be used to generate extrapolated data for the missing pixels of the target patches. In some embodiments, target patch may be initialized using standard methods such as nearest neighbor extrapolation. This extrapolation involves replacing the missing pixels of the image by the pixels of the nearest neighbor.

Since there is a lesser likelihood of finding similar anatomical structures far away from the target patch, the search for the missing pixels may be limited to regions near the target patch. At step 302, one or more candidate patches may be identified in the rows adjacent to the target patch. In one embodiment, candidate patches may be identified from the region within a predetermined number of rows from the target patch. In addition, candidate patches may comprise pixel data of the previously extrapolated rows. Pixel data from the candidate patches may be used to fill the target patch.

At step 304, one or more spatial correlation values are computed. These values represent the correlation between the target patch and the candidate patches. In one embodiment, computing spatial correlation values comprises computing a cost function based on mean square error between the target patch and the candidate patches.

The candidate patch with the maximum spatial correlation value is selected as the source patch at step 306. In one embodiment, the candidate patch, which provides lowest error between the target patch and the candidate patches, may be selected as the source patch. Pixel data from the source patch may be used for filling the target patch.

At step 308, extrapolated data may be generated for the pixels of the target patch. Specifically, extrapolated data may be generated based on the pixels of the source patch. The process 300 may be repeated for extrapolating all the rows present in the target patch. Further, all the target patches of the CT projection may be similarly extrapolated. The extrapolated projection data may be combined with the measured projection data to obtain a complete CT projection.

In various embodiments, the order in which the target patches are extrapolated may be configured to ensure the propagation of linear structures in the image. For example, the target patches adjacent to linear structures may be given higher filling priority. In various other embodiments, the filling order may be dynamically selected.

An unwanted DC shift may be present in the reconstructed image obtained by the process 300. In one embodiment, the process 300 may further comprise correcting the DC shift in the reconstructed image. For this, the process 300 comprises computing a Fourier transform of the extrapolated row of the target patch and another Fourier transform of the one or more rows adjacent to the target patch. One of the Fourier transforms may be analyzed to identify a DC term and some low frequency terms that may need correction. For correcting this, the identified DC term and the low frequency terms of one of the Fourier transforms are replaced with corresponding DC term and low frequency terms of another of the Fourier transforms. Accurate reconstructed image may be obtained upon completion of the DC shift correction process.

FIG. 4 illustrates example candidate, source, and target patches used for projection extrapolation, in accordance with one embodiment. Projection 400 may be divided into target patches 402, source patches 404, and candidate patches 406. The projection 400 comprises 256 rows of measured or available data and 20 extrapolated rows (10 rows on either side of the measured data). The top 10 rows and the bottom 10 rows illustrate rows extrapolated using the process 300.

FIG. 5 is a flowchart illustrating an example process of projection extrapolation, in accordance with another embodiment. The process 500 illustrates an extrapolation approach which computes the correlation along different angles and extrapolates along the direction of highest correlation. Since the correlation profiles can be simultaneously computed for all pixels in a row and several rows can be extrapolated simultaneously, computation time may be reduced.

At step 502, one or more directional vector templates may be generated for a pixel of the target patch. Directional vector templates are used to define the target patch. Directional vector templates may comprise the pixels of the target patch. In one embodiment, directional vector templates may be generated by shifting the rows in the available sinogram adjacent to the target patch. The method of generating the vector templates is shown in FIG. 6.

At step 504, spatial correlation values between the directional vector templates and the measured CT projection pixels in the rows adjacent to the target patch may be computed. Based on these values, a correlation profile may be generated. Further, information regarding the direction of maximum correlation may be obtained from the correlation profile.

In one embodiment, extrapolated values between the directional vector templates and the measured CT projection pixels in the rows adjacent to the target patch may be computed. Thus, a set of angle dependent extrapolated values may be obtained for each pixel of the target patch. To consider all the directions, a correlation weight may be assigned to each of the extrapolated values. At step 506, weighted average of the extrapolation values is computed.

At step 508, extrapolated value for the pixel of the target patch may be obtained by using the weighted average obtained at step 506. In an alternative embodiment, the extrapolated value for the pixel may be obtained by choosing the direction of maximum correlation and selecting the extrapolated value in the chosen direction.

FIG. 6 illustrates an example process of projection extrapolation using directional vector templates, in accordance with one embodiment. A projection 602, comprising the rows containing the measured data, is shown. Now, a row is to be extrapolated at the bottom side of the image 602. For this, consider a pixel 'x' from the row to be extrapolated as shown in the FIG. 6. Directional vector templates with various angles are generated for the pixel 'x'. Referring to image 602, arrows (a), (b), (c), and (d) denote the directions for which the directional vector templates are generated. In one embodiment, a row-shift approach may be used to generate the directional vector templates as shown in image 608. Similar vector templates may be generated by shifting one or more rows.

Spatial correlations values between the directional vector templates and the measured projection data are computed. A correlation profile 604 may be generated based on the computed values. Referring to correlation profile 604, a peak is obtained between the vector templates (b) and (c). This is because the gradient of the structure in the image 602 above the pixel 'x' falls between arrows (b) and (c). Thereafter, extrapolation values are calculated for the pixel 'x'. In one embodiment, a vector template providing the maximum correlation value (i.e. peak) may be used to compute the extrapolation value. In another embodiment, extrapolation values may be computed using each of the vector templates and a weighted sum of the extrapolation values may be computed as shown in graph 606.

FIG. 7 is a flowchart illustrating an example process of projection extrapolation, in accordance with another embodiment. The process 700 may be used for example to generate extrapolated data for the target patch. At step 702, a warping function between the target patch and the source patch may be computed. Warping function provides a mapping between two patches from the CT projection such that a predetermined cost function is minimized. In various embodiments, measured projection data may be used for learning the warping function. The method of computing a warping function is shown in FIG. 8.

Based on the warping function, the source patch is warped at step 704. The projection data of the source patch is warped to generate warped source patch. This results in alignment of the source patch with the target patch. Now, the target patch may be extrapolated along the aligned source patches at step 706. More specifically, warped data may be generated for the target patch based on the data of the warped source patch.

At step 708, warped data of the target patch is unwarped to obtain extrapolated data. Warping function may be used to facilitate the process of unwarping the target patch. Further, the extrapolated data may be combined with the measured projection data to generate a complete volume image.

FIG. 8 illustrates an example process using a warping function for projection extrapolation, in accordance with one embodiment. Warping function provides optimal mapping between a row from source patch and a row from the target patch. Measured projection data is used to compute the warping function.

In one embodiment, dynamic programming algorithms may be used to obtain the warping function between the target patch and the source patch. As in dynamic programming, the complete process of obtaining the solution is divided into various stages. Solutions are obtained for each stage and combined to arrive at an overall solution to the problem. Referring to FIG. 8, consider two sets of rows r1 and r2, each set comprising N rows of the projection data. The algorithm provides a mapping between the two sets of rows such that a predetermined cost function is minimized. In one embodiment, mean square error between the two sets of rows may be minimized.

The various embodiments and/or components, for example, the modules or components and controllers therein, also may be implemented as part of one or more computers or processors. The computer or processor may comprise a computing device, an input device, a display unit and an interface, for example, for accessing the Internet. The computer or processor may also comprise a microprocessor. The microprocessor may be connected to a communication bus. The computer or processor may also comprise a memory. The memory may comprise random access memory (RAM) and read only memory (ROM). The computer or processor further may comprise a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" means any processor-based or microprocessor-based system comprising systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be an information source or a physical memory element within a processing machine.

The set of instructions may comprise various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may comprise modular programming in the form of object-oriented programming. The processing of input data by the processing machine may be in response to operator commands, or in response to results of previous processing, or in response to a request made by another processing machine.

As used herein, the terms "software" and "firmware" are interchangeable, and comprise any computer program stored in memory for execution by a computer, comprising RAM memory, ROM memory, EPROM memory, EEPROM memory, and non-volatile RAM (NVRAM) memory. The above memory types are exemplary only, and are thus not limiting as to the types of memory usable for storage of a computer program.

The invention claimed is:

1. A method comprising:
   receiving, at an extrapolation processor, a CT projection for extrapolation;
   selecting a target patch comprising at least one pixel of a row to be extrapolated;
   forming an initialized target patch by setting the at least one pixel to be either zero or set equal to a neighboring pixel;
   generating a correlation profile between the initialized target patch and one or more source patches, wherein the source patches comprise measured pixels in the CT projection in one or more rows adjacent to the target patch and not including any area of the target patch; and
   generating projection data for the at least one pixel of the target patch based on the correlation profile and the measured pixels of at least one of the one or more source patches.

2. The method of claim 1, wherein generating a correlation profile comprises:
   identifying one or more candidate patches in the one or more rows adjacent to the target patch; and
   computing one or more spatial correlation values between the target patch and the one or more candidate patches.

3. The method of claim 2, wherein generating the projection data comprises:
   identifying a source patch from the one or more candidate patches based on a maximum of the one or more spatial correlation values; and
   extrapolating the at least one pixel of the target patch based on corresponding pixels in the source patch.

4. The method of claim 3 further comprising:
   computing a Fourier transform of one or more extrapolated rows of the target patch;
   computing another Fourier transform of the one or more rows adjacent to the target patch;
   identifying a DC term and at least one low frequency term from one of the Fourier transforms; and
   replacing the DC term and the at least one low frequency term with a DC term and corresponding low frequency terms of another of the Fourier transforms.

5. The method of claim 1, wherein generating a correlation profile comprises:
generating one or more directional vector templates, wherein the one or more directional vector templates comprise the pixel of the target patch; and
computing one or more spatial correlation values between the one or more directional vector templates and measured CT projection pixels in the one or more rows adjacent to the target patch.

6. The method of claim 5, wherein generating the projection data comprises:
computing a weighted average of the one or more extrapolation values; and
extrapolating the at least one pixel of the target patch based on the weighted average.

7. The method of claim 1, wherein generating a correlation profile comprises:
computing a warping function between the target patch and the source patch.

8. The method of claim 7, wherein generating the projection data comprises:
warping the source patch based on the warping function, to align the source patch with the target patch;
extrapolating the target patch based on the warped source patch; and
unwarping the target patch based on the warping function.

9. The method of claim 7, wherein the warping function between the target patch and source patch is computed using dynamic programming.

10. A system comprising:
at least one processor;
a non-transitory computer readable storage medium operatively coupled to the at least one processor, wherein the non-transitory computer readable storage medium contains computer program code that is operative to cause the at least one processor to:
receive a CT projection for extrapolation;
select a target patch comprising at least one pixel of a row to be extrapolated;
form an initialized target patch by setting the at least one pixel in the target patch to be equal to a neighboring pixel;
generate a correlation profile between the initialized target patch and one or more source patches, wherein the source patches comprise measured pixels in the CT projection in one or more rows adjacent to the target patch; and
generate projection data for the at least one pixel of the target patch based on the correlation profile and the measured pixels of at least one of the source patches.

11. The system of claim 10 wherein the non-transitory computer readable storage medium contains the computer program code that is further operative to cause the at least one processor to:
identify one or more candidate patches in the one or more rows adjacent to the target patch;
compute one or more spatial correlation values between the target patch and the one or more candidate patches.

12. The system of claim 11 wherein the non-transitory computer readable storage medium contains computer program code that is further operative to cause the at least one processor to:
identify a source patch from the one or more candidate patches based on a maximum of the one or more spatial correlation values; and
extrapolate the at least one pixel of the target patch based on corresponding pixels in the source patch.

13. The system of claim 10 wherein the non-transitory computer readable storage medium contains computer program code that is further operative to cause the at least one processor to:
compute a Fourier transform of one or more extrapolated rows of the initialized target patch;
compute another Fourier transform of the one or more rows adjacent to the target patch;
identify a DC term and at least one low frequency term from one of the Fourier transforms; and
replace the DC term and the at least one low frequency term with a DC term and corresponding low frequency terms of another of the Fourier transforms.

14. The system of claim 10 wherein the non-transitory computer readable storage medium contains computer program code that is further operative to cause the at least one processor to:
generate one or more directional vector templates, wherein the one or more directional vector templates comprise the pixel of the target patch; and
compute one or more spatial correlation values between the one or more directional vector templates and measured CT projection pixels in the one or more rows adjacent to the target patch.

15. The system of claim 14 wherein the non-transitory computer readable storage medium contains computer program code that is further operative to cause the at least one processor to:
compute a weighted average of the one or more extrapolation values; and
extrapolate the at least one pixel of the target patch based on the weighted average.

16. The system of claim 10 wherein the non-transitory computer readable storage medium contains computer program code that is further operative to cause the at least one processor to:
compute a warping function between the target patch and the source patch.

17. The system of claim 16 wherein the non-transitory computer readable storage medium contains computer program code that is further operative to cause the at least one processor to:
warp the source patch based on the warping function, to align the source patch with the target patch;
extrapolate the target patch based on the warped source patch; and
unwarp the target patch based on the warping function.

18. The system of claim 16, wherein the non-transitory computer readable storage medium contains computer program code that is further operative to cause the at least one processor to:
compute the warping function between the target patch and source patch using dynamic programming.

19. A non-transitory computer readable medium encoded with computer-executable instructions adapted to extrapolate CT projections, wherein the computer-executable instructions, when executed, cause one or more processors to:
receive a CT projection for extrapolation;
select a target patch comprising at least one pixel of a row to be extrapolated;
create an initialized target patch by setting the at least one pixel equal in value to a neighborhood pixel;
generate a correlation profile between the initialized target patch and one or more source patches, wherein the source patches comprise measured pixels in the CT projection in one or more rows adjacent to the target patch; and generate projection data for the at least one pixel of the target patch based on the correlation profile and the measured pixels of at least one of the source patches.

20. The non-transitory computer readable medium of claim 19 further comprising computer executable instructions to cause the one or more processors to:
identify one or more candidate patches in the one or more rows adjacent to the target patch;
compute one or more spatial correlation values between the target patch and the one or more candidate patches.

21. The non-transitory computer readable medium of claim 20 further comprising computer executable instructions to cause the one or more processors to:
identify a source patch from the one or more candidate patches based on a maximum of the one or more spatial correlation values; and
extrapolate the at least one pixel of the target patch based on corresponding pixels in the source patch.

22. The non-transitory computer readable medium of claim 21 further comprising computer executable instructions to cause the one or more processors to:
compute a Fourier transform of one or more extrapolated rows of the target patch;
compute another Fourier transform of the one or more rows adjacent to the target patch;
identify a DC term and at least one low frequency term from one of the Fourier transforms; and
replace the DC term and the at least one low frequency term with a DC term and corresponding low frequency terms of another of the Fourier transforms.

23. The non-transitory computer readable medium of claim 20 further comprising computer executable instructions to cause the one or more processors to:
generate one or more directional vector templates, wherein the one or more directional vector templates comprise the pixel of the target patch; and
compute one or more spatial correlation values between the one or more directional vector templates and measured CT sinogram pixels in the one or more rows adjacent to the target patch.

24. The non-transitory computer readable medium of claim 23 further comprising computer executable instructions to cause the one or more processors to:
compute a weighted average of the one or more extrapolation values; and
extrapolate the at least one pixel of the target patch based on the weighted average.

25. The non-transitory computer readable medium of claim 20 further comprising computer executable instructions to cause the one or more processors to:
compute a warping function between the target patch and the source patch.

26. The non-transitory computer readable medium of claim 25 further comprising computer executable instructions to cause the one or more processors to:
warp the source patch based on the warping function, to align the source patch with the target patch;
extrapolate the target patch based on the warped source patch; and
unwarp the target patch based on the warping function.

27. The non-transitory computer readable medium of claim 25 further comprising computer executable instructions to cause the one or more processors to:
compute the warping function between the target patch and source patch using dynamic programming.

* * * * *